_United States Patent_ [19]

Henry et al.

[11] 4,125,704

[45] Nov. 14, 1978

[54] PHENYL-SUBSTITUTED RUBIDAZONE ANALOGS

[75] Inventors: David W. Henry, Chapel Hill, N.C.; George L. Tong, Cupertino, Calif.

[73] Assignee: SRI International, Menlo Park, Calif.

[21] Appl. No.: 833,165

[22] Filed: Sep. 14, 1977

[51] Int. Cl.$^2$ .............................................. C07G 3/00
[52] U.S. Cl. ...................................... 536/4; 424/180; 536/17
[58] Field of Search ................................... 536/4, 17 A

[56] References Cited

U.S. PATENT DOCUMENTS

| 3,957,755 | 5/1976 | Jolles | 536/4 |
| 3,965,088 | 6/1976 | Jolles | 536/4 |

_Primary Examiner_—Ethel G. Love
_Attorney, Agent, or Firm_—Donovan J. De Witt

[57] ABSTRACT

Rubidazone analogs wherein the phenyl group is substituted by one of 4-phenyl, 4-chloro, 3,4-dichloro or 3-nitro, said compounds having high antitumor activity coupled with desirably low cardiotoxicity.

5 Claims, No Drawings

PHENYL-SUBSTITUTED RUBIDAZONE ANALOGS

BACKGROUND OF INVENTION

The invention described herein was made in the course of or under a contract with the U.S. Department of Health, Education, and Welfare.

PRIOR ART

The prior art teaches the derivative of rubidazone wherein the phenyl group is substituted by 4-methoxy (G. Jolles, R. Maral, M. Messer and G. Ponsinet, *Antitumor Activity of Daunorubicin Derivatives*, pp 237–241, (Chemotherapy, Vol. 8, Cancer Chemotherapy II, Plenum Press, New York and London (1975)). Biological test data with reference to this compound are included in the table given below. It is to be noted that the compound has the same relatively low mean cumulative cardiotoxicity dose (24 mg/kg) as does rubidazone.

SUMMARY OF INVENTION

The present invention relates to the discovery of novel rubidazone analogs having the structure

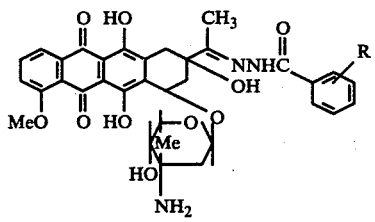

where R represents 4-phenyl (I), 4-chloro (II), 3,4-dichloro (III) or 3-nitro (IV), together with the pharmaceutically acceptable salts of each of these compounds (I)–(IV). A method for the preparation of each of these compounds is set forth in the examples. The biological test data presented in the table given below demonstrate that all four of the compounds of the present invention have good antitumor activity (tested against leukemia P388 in mice) coupled with a high minimum cumulative cardiotoxicity dose (MCCD). In the latter respect compounds (I)–(III) have particularly good MCCD values, with compound (II), having the highest level of all. The higher the MCCD value, the lower the cardiotoxicity.

The compound of the present invention may also be named as derivatives of daunomycin, as follows:
Daunomycin 4-phenylbenzhydrazone hydrochloride (I),
Daunomycin 4-chlorobenzhydrazone hydrochloride (II),
Daunomycin 3,4-dichlorobenzhydrazine hydrochloride (III) and
Daunomycin 3-nitrobenzhydrazone hydrochloride (IV). The preparation of each of the foregoing compounds is described in the following examples:

EXAMPLE I

Daunomycin 4-Phenylbenzhydrazone Hydrochloride (I)

A solution of 1.13 g (2.0 mmole) of daunomycin hydrochloride and 0.85 g (4.0 mmole) of 4-phenylbenzhydrazide in 75 ml of methanol was stirred at room temperature in the dark for 4 days. After concentrating to about 10 ml, the reaction mixture was stirred and slowly diluted with 100 ml of acetonitrile. The resulting precipitate was collected and washed with 3 × 5 ml of acetonitrile to afford 1.174 g of the hydrazone (I) with a small amount of 4-phenylbenzhydrazide. The mother liquors were evaporated; the residue was dissolved in 5 ml of methanol and the stirred solution was diluted with 75 ml of acetonitrile to give an additional 0.211 g of (I). The two crops of (I) were combined and dissolved in 5 ml of methanol; the solution was stirred and 75 ml of acetonitrile were added dropwise. The resulting precipitate was triturated in the methanol-acetonitrile mixture overnight and then collected, washed with acetonitrile and dried at room temperature/0.1 mm/15 hr to yield the hydrazone hydrochloride (I), 1.253 g (81%) mp 205°–208° decomposed.

| Anal. calcd. for $C_{40}H_{39}N_3O_{10} \cdot HCl \cdot H_2O$ | | | | |
|---|---|---|---|---|
| | C | H | $Cl^{\ominus}$ | N |
| | 61.89 | 5.45 | 4.57 | 5.41 |
| Found | 62.14 | 5.51 | 4.78 | 5.32 |

EXAMPLE II

Daunomycin 4-Chlorobenzhydrazone Hydrochloride (II)

A solution of 0.564 g (1.0 mmole) of daunomycin hydrochloride and 0.512 g (3.0 mmole) of 4-chlorobenzhydrazide in 20 ml of methanol was stirred at room temperature in the dark for 3 days during which time the product (II) precipitated. The product was collected, washed with 4 × 1 ml of methanol and dried at room temperature/0.1 mm/15 hr to yield 0.570 g (79%) of a red-orange powder (II), mp 247°–250° decomposed.

| Anal. calc. for $C_{34}H_{34}ClN_3O_{10} \cdot HCl$ | | | | |
|---|---|---|---|---|
| | C | H | Cl | N |
| | 56.99 | 4.92 | 9.90 | 5.86 |
| Found | 57.00 | 5.03 | 9.51 | 5.80 |

EXAMPLE III

Daunomycin 3,4-Dichlorobenzhydrazone Hydrochloride (III)

A solution of 0.564 g (1.0 mmole) of daunomycin hydrochloride and 0.410 g (2.0 mmole) of 3,4-dichlorobenzhydrazide in 20 ml of methanol was stirred at room temperature in the dark for 3 days. The reaction mixture was stirred and slowly diluted with 100 ml of acetonitrile; the clear solution was allowed to stand at room temperature in the dark overnight. The resulting precipitate was collected, washed with 5 × 1 ml of methanol-acetronitrile (1:5) and dried at room temperature/0.1 mm/16 hr to give 0.619 g (82%) of the hydrazone (III), mp 249°–251° decomposed.

| Anal. calc. for $C_{34}H_{33}Cl_2N_3O_{10} \cdot HCl$ | | | | |
|---|---|---|---|---|
| | C | H | Cl | N |
| | 54.38 | 4.56 | 14.16 | 5.60 |
| Found | 54.59 | 4.61 | 13.78 | 5.85 |

EXAMPLE IV

Daunomycin 3-Nitrobenzyhydrazone Hydrochloride (IV)

A solution of 0.564 g (1.0 mmole) of daunomycin hydrochloride and 0.362 g (2.0 mmole) of 3-nitrobenzhydrazide in 25 ml of methanol was stirred at room temperature in the dark for 3 days during which time the hydrazone (IV) precipitated. The prepcipitate was collected, washed with 4 × 1 ml of methanol and dried at room temperature/0.1 mm/16 hr to afford an orange powder (IV), 0.628 g (86%), mp 247°–249° decomposed.

| Anal. calcd. for $C_{34}H_{34}N_4O_{12}$ . HCl | | | | |
|---|---|---|---|---|
| | C | H | $Cl^\theta$ | N |
| | 56.16 | 4.85 | 4.88 | 7.71 |
| Found | 56.24 | 4.89 | 4.89 | 7.85 |

It will be noted that the compounds of the invention are prepared in the form of acid addition salts with the free —$NH_2$ group of the compounds. The compounds are preferably employed in such salt form since they then have adequate solubility in water. However, they can be employed in the non-salt form if so desired. These acid addition salts (shown herewith as those of HCl) are preferably the pharmaceutically acceptable, non-toxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicylic acids, and organic sulphonic acids, for example, methane-sulphonic and toluene-p-sulphonic acids. Acid addition salts of the present invention can be converted into the free compound according to known methods, for example, by treatment with a base, such as an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example sodium, potassium or calcium carbonate or hydrogen carbonate; with ammonia; or with a hydroxyl ion exchange resin, or with any other suitable reagent. An acid addition salt may also be converted into another acid addition salt according to known methods; for example, a salt with an inorganic acid may be treated with a metal salt, for example, a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation. The compounds of this invention can be formulated as novel pharmaceutical preparations together with conventional pharmaceutical organic or inorganic carrier materials suitable for internal administration. Such preparations can be administered parenterally or orally, the dosages to be adjusted according to individual requirements. The novel pharmaceutical compositions can contain such conventional organic or inorganic inert carrier materials as water, gelatin, lactose, starch, magnesium stearate, talc, vegetable oils, gums polyalkylene glycols, vaseline or the like. The pharmaceutical preparations can be in the conventional solid forms such as tablets, dragees, suppositories, capsules or in conventional liquid form such as solutions, suspensions of emulsions. The pharmaceutical compositions can be submitted to conventional pharmaceutical expedients such as sterilization and/or can contain conventional pharmaceutical additives such as preservatives, stabilizing agents, wetting agents, emulsifying agents, salts for adjusting the osmotic pressure, buffers or the like. They also can contain other therapeutically useful materials.

BIOLOGICAL TESTS

Biological testing data for the compounds of this invention, as the HCl salts, and for rubidazone and the methoxy derivative of the prior art are presented in the table given below. Said data were obtained when these compounds were tested against lymphocytic leukemia P388 implanted in mice under the auspices of the NCI and according to protocols which use the increased survival time of treated animals compared to controls as the measure of antitumor efficacy. Also included in the table are results obtained in the cardiotoxic evaluation of the indicated compounds in a reproducible screening system employing the rat, the data so obtained being referred to as the minimum cumulative cardiotoxic dose (MCCD). In these tests the rat model employs as end point the characteristic electrocardiographic changes that follow repeated administration of cardiotoxic anthracycline derivatives.

TABLE

| | | | Activity vs Leukemia P388 in MIce[c,d] | | | |
|---|---|---|---|---|---|---|
| | | Minimum[b] Cumulative Cardiotoxic | qd 1–9 | | $q^4d$ 5,9,13 | |
| Compound | NSC[a] No. | Dose mg/kg | Increased Survival Time % T/C | Optimum Dose mg/kg | Increased Survival Time % T/C | Optimum Dose mg/kg |
| Rubidazone | 164011 | 24 | 192 | 4.0 | 183 | 37.5 |
| 4-methoxy derivative | 219976 | 24 | 213 | 2.0 | 145 | 24 |
| I 4-phenyl | 236672 | 40 | 165 | 2.0 | 149 | 24 |
| II 4-chloro | 219977 | 48 | 210 | 2.0 | 143 | 24 |
| III 3,4-dichloro | 221266 | 40 | 208 | 2.0 | — | — |
| IV 3-nitro | 221265 | 32 | 188 | 2.0 | 149 | 25 |

[a]Accession number of the National Cancer Institute.
[b]Assay described in G. Zbinden and E. Brandle, Cancer Chemo. Rpts., Part 1, 59, 707 (1975).
[c]Ip P388 murine leukemia treated ip on QD1-9 and Q4D 5, 9, 13 schedules according to standard NCI protocols. Assay described in R. I. Geran, N. H. Greenberg, M. M. MacDonald, A. M. Schumacker and B. J. Abbott, Cancer Chemother. Rep., Part 3, 3 (No. 2), 9 (1972), Protocol 1,200. T/C = ratio of survival time of treated mice to that of untreated controls times 100. Untreated controls survive about 9 days.
[d]Average of 2 – 3 tests.

We claim:
1. Compounds having the structure

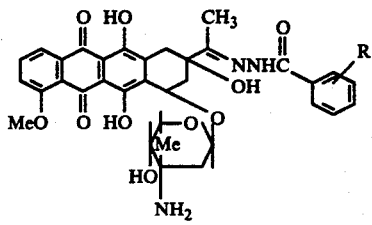

wherein R represents 4-phenyl, 4-chloro, 3,4-dichloro or 3-nitro, and the pharmaceutically acceptable salts of these compounds.

2. The compound of claim 1 which is daunomycin 4-phenylbenzhydrazone hydrochloride.

3. The compound of claim 1 which is daunomycin 4-chlorobenzhydrazone hydrochloride.

4. The compound of claim 1 which is daunomycin 3,4-dichlorobenzhydrazone hydrochloride.

5. The compound of claim 1 which is daunomycin 3-nitrobenzhydrazone hydrochloride.